(12) United States Patent
McAuley et al.

(10) Patent No.: US 8,100,126 B2
(45) Date of Patent: Jan. 24, 2012

(54) BREATHING ASSISTANCE APPARATUS

(76) Inventors: Alastair Edwin McAuley, Auckland (NZ); Christopher Earl Nightingale, London (GB); Aidan Mark Shotbolt, Dunedin (NZ); Ivan Milivojevic, London (GB); Lewis George Gradon, Auckland (NZ); Mark Joseph Haycock, Basel (CH); Nicholas Charles Alan Smith, Hamilton (NZ); Daniel Mahon, Christchurch (NZ)

( * ) Notice: Subject to any disclaimer, the term of this patent is extended or adjusted under 35 U.S.C. 154(b) by 1206 days.

(21) Appl. No.: 11/368,004

(22) Filed: Mar. 3, 2006

(65) Prior Publication Data

US 2006/0237018 A1    Oct. 26, 2006

Related U.S. Application Data (60) Continuation-in-part of application No. 10/456,661, filed on Jun. 6, 2003, now abandoned, which is a division of application No. 10/297,951, filed as application No. PCT/NZ01/00110 on Jun. 14, 2001, now abandoned, application No. 11/368,004, which is a continuation-in-part of application No. PCT/NZ2004/000194, filed on Aug. 20, 2004.

(30) Foreign Application Priority Data

| Jun. 14, 2000 | (NZ) | ......................................... 505154 |
| Jun. 14, 2000 | (NZ) | ......................................... 505156 |
| Dec. 20, 2000 | (NZ) | ......................................... 509039 |
| Mar. 12, 2001 | (NZ) | ......................................... 510520 |
| Sep. 3, 2003 | (NZ) | ......................................... 528029 |

(51) Int. Cl.
*A62B 18/08* (2006.01)
*A62B 18/02* (2006.01)

(52) U.S. Cl. ......... 128/206.24; 128/206.28; 128/206.21; 128/205.25; 128/200.24

(58) Field of Classification Search .................. 128/857, 128/863, 200.24, 201.22, 201.23, 202.27, 128/203.29, 205.25, 206.21, 206.27, 206.28, 128/207.11
See application file for complete search history.

(56) References Cited

U.S. PATENT DOCUMENTS

| 2,245,658 | A | 6/1941 | Erickson |
| 2,931,356 | A | 4/1960 | Schwarz |
| 3,303,845 | A | 2/1967 | Detmer, III |
| 3,330,273 | A | 7/1967 | Bennett |
| 3,680,555 | A | 8/1972 | Warncke |

(Continued)

FOREIGN PATENT DOCUMENTS

| CA | 1039144 | 9/1978 |

(Continued)

OTHER PUBLICATIONS

Sep. 21, 2001 International Search Report for Application No. PCT/NZ01/00110 filed on Jun. 14, 2001.

*Primary Examiner* — Justine Yu
*Assistant Examiner* — Annette Dixon
(74) *Attorney, Agent, or Firm* — Knobbe, Martens, Olson & Bear, LLP.

(57) ABSTRACT

The present invention is a mask for the delivery of gases to a patient. The mask has a hollow body and a cushion that seals against the user's face. The cushion is comprised of an inner resilient cushion and an outer flexible sheath. The cushion preferably extends below the patient's chin when in use.

22 Claims, 12 Drawing Sheets

U.S. PATENT DOCUMENTS

| | | | |
|---|---|---|---|
| 3,747,598 A | 7/1973 | Cowans | |
| 3,815,596 A * | 6/1974 | Keener et al. | 128/205.17 |
| 3,890,966 A | 6/1975 | Aspelin et al. | |
| 3,982,532 A | 9/1976 | Halldin et al. | |
| 4,069,516 A * | 1/1978 | Watkins, Jr. | 2/428 |
| 4,201,206 A | 5/1980 | Kuehn et al. | |
| 4,226,234 A | 10/1980 | Gunderson | |
| 4,665,570 A * | 5/1987 | Davis | 2/428 |
| 4,706,683 A | 11/1987 | Chilton et al. | |
| 4,794,921 A * | 1/1989 | Lindkvist | 128/203.29 |
| 4,907,584 A * | 3/1990 | McGinnis | 128/206.24 |
| 4,971,051 A * | 11/1990 | Toffolon | 128/206.26 |
| 5,031,612 A | 7/1991 | Clementi | |
| 5,042,478 A | 8/1991 | Kopala et al. | |
| 5,143,061 A * | 9/1992 | Kaimer | 128/206.24 |
| 5,243,971 A * | 9/1993 | Sullivan et al. | 128/205.25 |
| 5,349,949 A * | 9/1994 | Schegerin | 128/206.24 |
| 5,438,978 A | 8/1995 | Hardester, III | |
| 5,438,981 A | 8/1995 | Starr et al. | |
| 5,517,986 A | 5/1996 | Starr et al. | |
| 5,570,689 A | 11/1996 | Starr et al. | |
| 5,592,938 A * | 1/1997 | Scarberry et al. | 128/206.24 |
| 5,647,344 A | 7/1997 | Turnbull | |
| 5,647,357 A * | 7/1997 | Barnett et al. | 128/206.24 |
| 5,724,965 A | 3/1998 | Handke et al. | |
| 5,758,642 A | 6/1998 | Choi | |
| 5,884,624 A * | 3/1999 | Barnett et al. | 128/206.24 |
| 6,112,746 A * | 9/2000 | Kwok et al. | 128/207.13 |
| 6,244,865 B1 | 6/2001 | Nelson et al. | |
| 6,397,847 B1 * | 6/2002 | Scarberry et al. | 128/206.24 |
| 6,412,487 B1 * | 7/2002 | Gunaratnam et al. | 128/206.24 |
| 6,460,539 B1 | 10/2002 | Japuntich et al. | |
| 6,467,482 B1 * | 10/2002 | Boussignac | 128/206.24 |
| 6,513,526 B2 * | 2/2003 | Kwok et al. | 128/206.24 |
| 6,532,961 B1 * | 3/2003 | Kwok et al. | 128/206.21 |
| 6,536,424 B2 | 3/2003 | Fitton | |
| 6,615,834 B2 | 9/2003 | Gradon et al. | |
| 6,634,358 B2 * | 10/2003 | Kwok et al. | 128/205.25 |
| D483,477 S | 12/2003 | Ankey et al. | |
| 6,679,257 B1 | 1/2004 | Robertson et al. | |
| 6,679,261 B2 | 1/2004 | Lithgow et al. | |
| 6,701,926 B2 | 3/2004 | Olsen et al. | |
| 6,736,139 B1 | 5/2004 | Wix | |
| 6,789,541 B2 | 9/2004 | Olsen et al. | |
| 6,820,617 B2 | 11/2004 | Robertson et al. | |
| 6,951,218 B2 * | 10/2005 | Gradon et al. | 128/205.25 |
| 6,997,186 B2 | 2/2006 | Robertson et al. | |
| 7,017,576 B2 | 3/2006 | Olsen et al. | |
| 7,219,669 B1 | 5/2007 | Lovell et al. | |
| 2003/0154978 A1 | 8/2003 | Gradon et al. | |
| 2003/0196659 A1 | 10/2003 | Gradon et al. | |
| 2008/0047557 A1 | 2/2008 | Gradon et al. | |
| 2008/0060657 A1 | 3/2008 | McAuley et al. | |
| 2008/0302366 A1 | 12/2008 | McGinnis et al. | |
| 2009/0223520 A1 | 9/2009 | McAuley et al. | |

FOREIGN PATENT DOCUMENTS

| | | |
|---|---|---|
| EP | 0 125 210 A1 | 11/1984 |
| EP | 1 245 250 A2 | 10/2002 |
| GB | 1 395 391 | 5/1975 |
| JP | 11-000397 | 1/1999 |
| JP | 2000-325481 | 11/2000 |
| RU | 2 186 597 C1 | 8/2002 |
| SU | 726692 | 9/1981 |
| WO | 85/03880 A1 | 9/1985 |
| WO | 98/04310 A1 | 2/1998 |
| WO | 98/34665 A1 | 8/1998 |
| WO | 00/57942 A1 | 10/2000 |
| WO | 00/74758 A1 | 12/2000 |
| WO | 00/78384 A1 | 12/2000 |
| WO | 01/26722 A1 | 4/2001 |
| WO | WO 01/95965 | 12/2001 |

* cited by examiner

BREATHING ASSISTANCE APPARATUS

This application is a continuation-in-part of Ser. No. 10/456,661, filed on Jun. 6, 2003, which is a divisional application of Ser. No. 10/297,951 (now abandoned), which was accorded a filing date under 35 U.S.C. §371 of Mar. 25, 2003, and entitled Breathing Assistance Apparatus which is the National Stage of International Application No. PCT/NZ01/00110 which has an international filing date of Jun. 14, 2001 and which was published in English on Dec. 20, 2001 under International Publication Number WO 01/95965. This application is also a continuation-in-part of International Application No. PCT/NZ04/00194 which has an international filing date of Aug. 20, 2004 and which was published in English on Mar. 10, 2005 under International Publication Number WO 2005/021075.

BACKGROUND OF THE INVENTION

1. Field of the Invention

This invention relates to the delivery of respiratory gases, and in particular to patient interfaces for providing gases to patients requiring respiratory therapy, such as the provisional of continuous positive airways pressure therapy to patients suffering from obstructive sleep apnoea (OSA).

2. Summary of the Prior Art

In the art of respiration devices, there are well known variety of respiratory masks that cover the nose and/or mouth of a human user in order to provide a continuous seal around the nasal and/or oral areas of the face such that gas may be provided at positive pressure within the mask for consumption by the user. The uses for such masks range from high altitude breathing (i.e., aviation applications) to mining and fire fighting applications, to various medical diagnostic and therapeutic applications.

One requisite of such respiratory masks has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

U.S. Pat. No. 5,243,971 and U.S. Pat. No. 6,112,746 are examples of prior art attempts to improve mask sealing.

In common with all attempts to improve the fit, sealing and user comfort is the need to avoid a concentrated flow of air at any portion of the respiratory tract. In particular with oral masks or mouthpieces it is a disadvantage of prior art devices that the oral cavity may become overly dehydrated by use of the device, causing irritation and possible later complications.

SUMMARY OF THE INVENTION

It is an object of the present invention to attempt to provide a patient interface that goes some way to overcoming the abovementioned disadvantages in the prior art or which will at least provide the industry with a useful choice.

Accordingly in one aspect the invention consists in a device for delivering a supply of gases to a user comprising:

a hollow body including a gases inlet and gases delivery aperture, said gases inlet in use in fluid communication with said supply of gases, a resilient cushion adapted to engage around or adjacent to the periphery of said gases delivery aperture, and a flexible sheath adapted to engage around or adjacent to the periphery of said gases delivery aperture between said resilient cushion and a user, said resilient cushion and said flexible sheath each including at least a portion shaped to approximate the facial contour of a user, said resilient cushion is adapted to deform substantially independently of said flexible sheath, Preferably said flexible sheath is of significantly higher density than that of said resilient cushion.

Preferably said resilient cushion is a foam cushion.

Preferably said flexible sheath is a sealing membrane substantially covering, and substantially thinner than, said resilient cushion.

Preferably said hollow body has a flange at least partially around the interior of said hollow body, said flange and said interior forming a cavity adapted to house in use a part of said resilient cushion.

Preferably the periphery of said gases delivery aperture and the periphery of said flexible sheath are fitted with corresponding connectors, whereby in use said flexible sheath is adapted to fit at least partially over the periphery of said hollow body, said corresponding connectors thereby in use holding said flexible sheath substantially in position on said hollow body, to assist in sealing said flexible sheath against the facial contours of a user.

Preferably said resilient cushion and said flexible sheath extends below a user's chin in use.

Preferably said hollow body is more rigid than said cushion.

Preferably the contours of said hollow body extend to enclose the nose and mouth of a user.

Preferably said hollow body extends below a user's chin.

Preferably said hollow body includes a flexible strap attached to it, the strap capable of sliding over said mask, said strap having two ends, each end of the strap attached to a headgear strap, the strap allowing said headgear straps to move without moving said mask.

Preferably said hollow body includes a plurality of flanges, said cushion retained within said flanges, said sealing sheath attached about the periphery of said hollow body and loosely attached about said cushion.

Preferably said cushion includes an indented section intended to ht over the bridge of the user's nose.

Preferably said cushion further includes a less indented section to seal around the part of the user's face under the nose and above the upper lip.

Preferably said device includes a forehead rest, said forehead rest adapted to rest against the forehead of the user.

Preferably said device further comprises headgear, said headgear secured around the back of the head of the user, the headgear exerting a restraining force on said forehead rest and said hollow body, said restraining force also acting on said cushion to provide effective sealing against the user's face.

Preferably said hollow body is constructed from a substantially rigid material, said hollow body also being substantially transparent.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

Preferred forms of the present invention will now be described with reference to the accompanying drawings.

DETAILED DESCRIPTION OF THE PREFERRED EMBODIMENTS

The present invention provides improvements in the delivery of CPAP therapy. In particular a patient interface is described which is quieter for the user to wear and reduces the side leakage as compared with the prior art. It will be appreciated that the patient interface as described in the preferred embodiment of the present invention can be used in respiratory care generally or with a ventilator but will now be described below with reference to use in a humidified CPAP system. It will also be appreciated that the present invention can be applied to any form of patient interface including, but not limited to, nasal masks, oral masks and mouthpieces.

Figure 1:
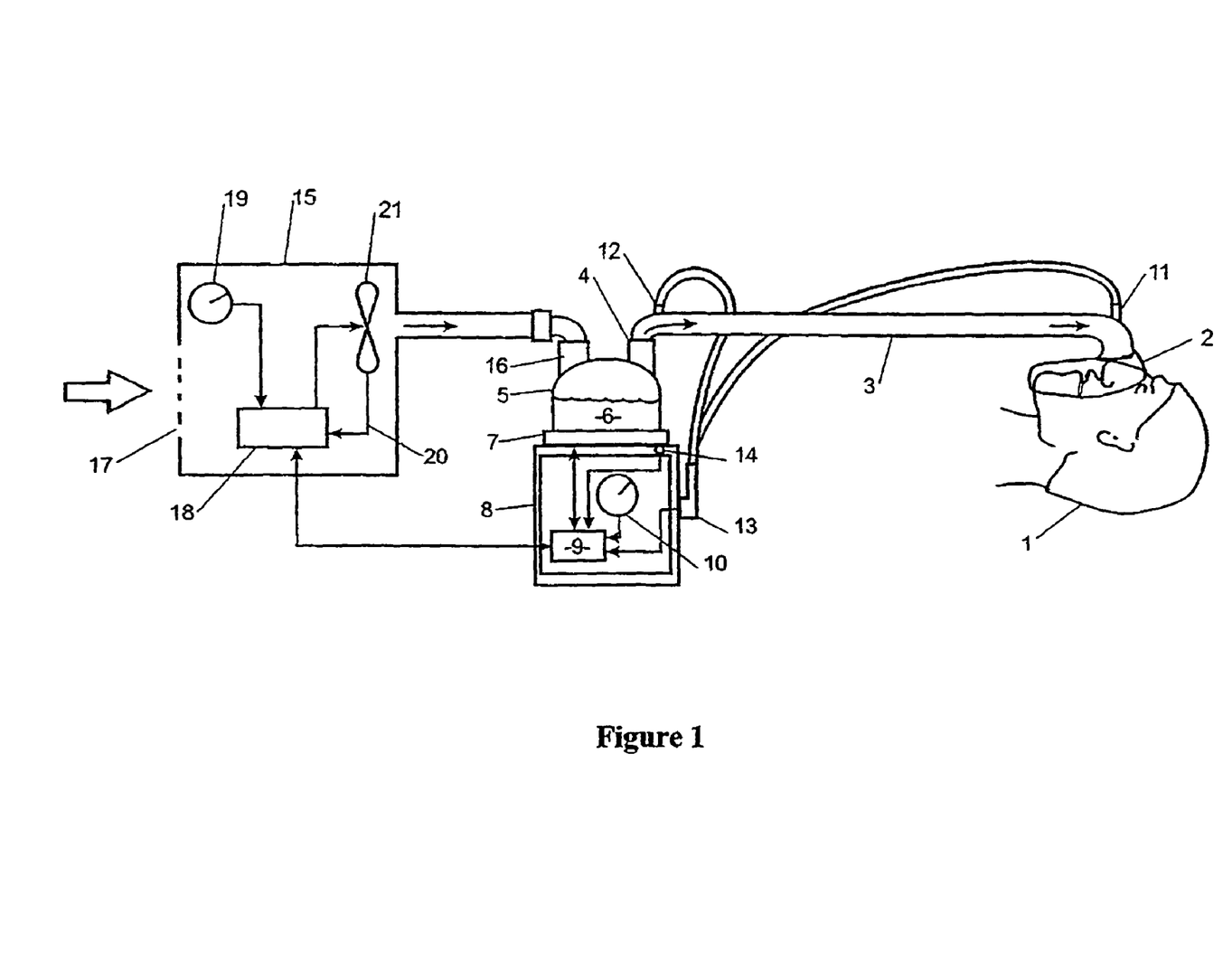
FIG. 1 is a block diagram of a humidified continuous positive airway pressure (system) as might be used in conjunction with the present invention.

With reference to FIG. 1 a humidified continuous positive airway pressure (CPAP) system is shown in which a patient 1 is receiving humidified and pressurised gases through a patient interface 2 connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. The inspiratory conduit 3 is connected to the outlet 4 of a humidification chamber 5 that contains a volume of water 6. The inspiratory conduit 3 may contain heater wires (not shown) which heat the walls of the conduit to reduce condensation of humidified gases within the conduit. The humidification chamber 5 is preferably formed from a plastics material and may have a highly heat conductive base (for example an aluminium base) which is in direct contact with a heater plate 7 of a humidifier 8. The humidifier 8 is provided with an electronic controller 9 which may comprise a microprocessor based controller executing computer software commands stored in associated memory.

The controller 9 receives input from sources such as dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, the controller 9 determines when (or to what level) to energise the heater plate 7 to heat the water 6 within the humidification chamber 5. As the volume of water 6 within the humidification chamber 5 is heated, water vapour begins to fill the volume of the chamber above the water's surface and is passed out of the humidification chamber 5 outlet 4 with the flow of gases (for example air) provided from the blower 15 that enters the chamber through the inlet 16. Exhaled gases from the patient's mouth are passed directly to ambient surroundings in FIG. 1.

A blower 15 is provided with variable speed fan 21 which draws air or other gases through a blower inlet 17. The speed of variable speed fan 21 is controlled by an electronic controller 18 (or alternatively the function of the controller 18 could carried out by the controller 9) in response to inputs from the controller 9 and a user set predetermined required value (preset value) of pressure or the fan speed via the dial 19.

Nasal Mask

Figure 2:
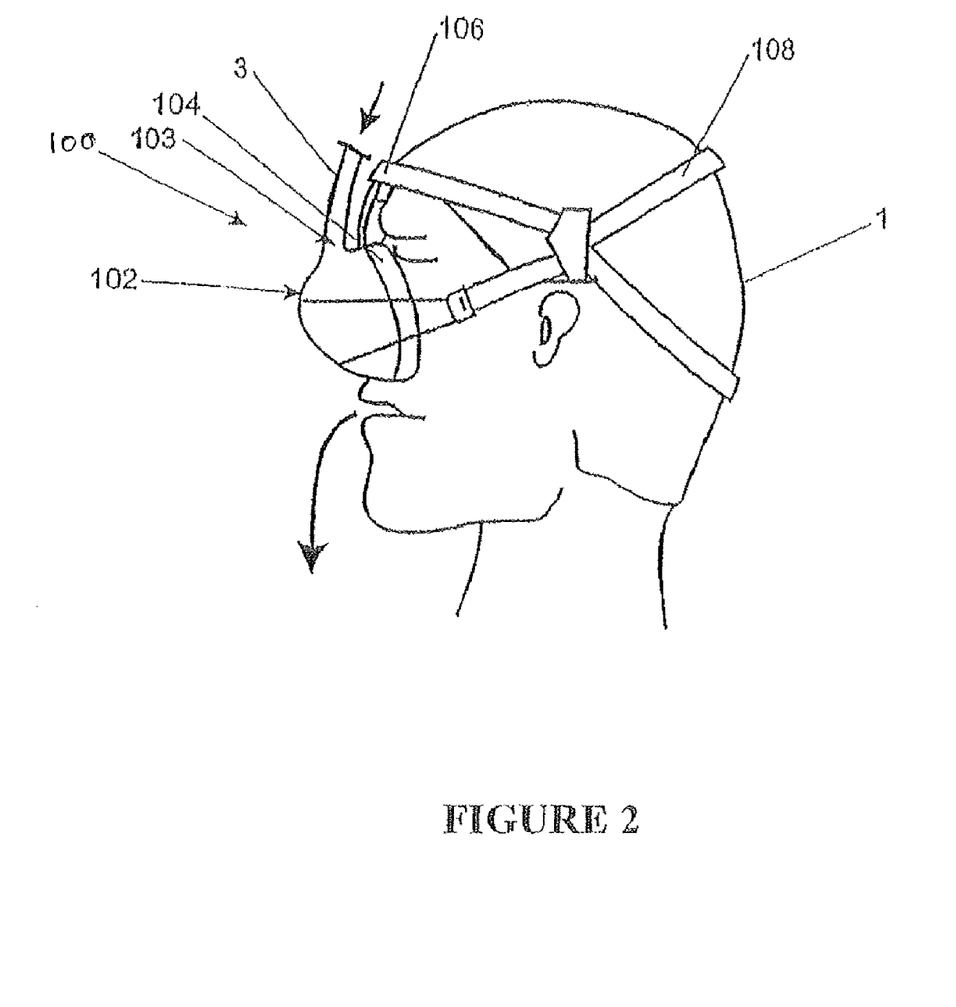
FIG. 2 is an illustration of the nasal mask in use according to a first embodiment of the present invention.

According to a first embodiment of the present invention a patient interface is shown in FIG. 2 as a nasal mask 100. The mask 100 includes a hollow body 102 with an inlet 103 connected to the inspiratory conduit 3. The mask 100 is positioned around the nose of the user 1 with the headgear 108 secured around the back of the head of the patient 1. The restraining force from the headgear 108 on the hollow body 102 and the forehead rest 106 ensures enough compressive force on the mask cushion 104, to provide an effective seal against the patient's face.

The hollow body 102 is constructed of a relatively inflexible material for example, polycarbonate plastic. Such a material would provide the requisite rigidity as well as being transparent and a relatively good insulator. The expiratory gases can be expelled through a valve (not shown) in the mask, a further expiratory conduit (not shown), or any other such method as is known in the art.

Mask Cushion

Figure 3:
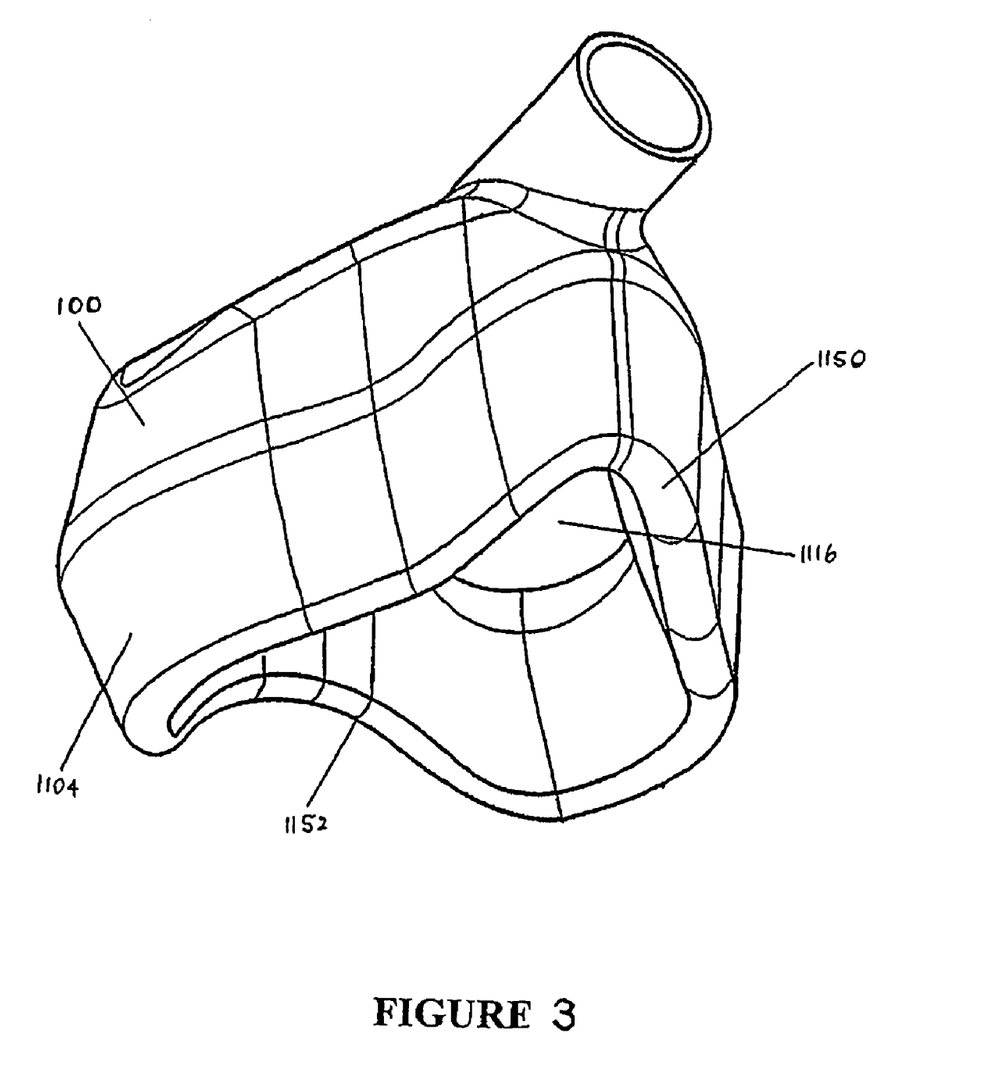
FIG. 3 shows a perspective view of an inner cushion of the mask of FIG. 2.
Figure 4:
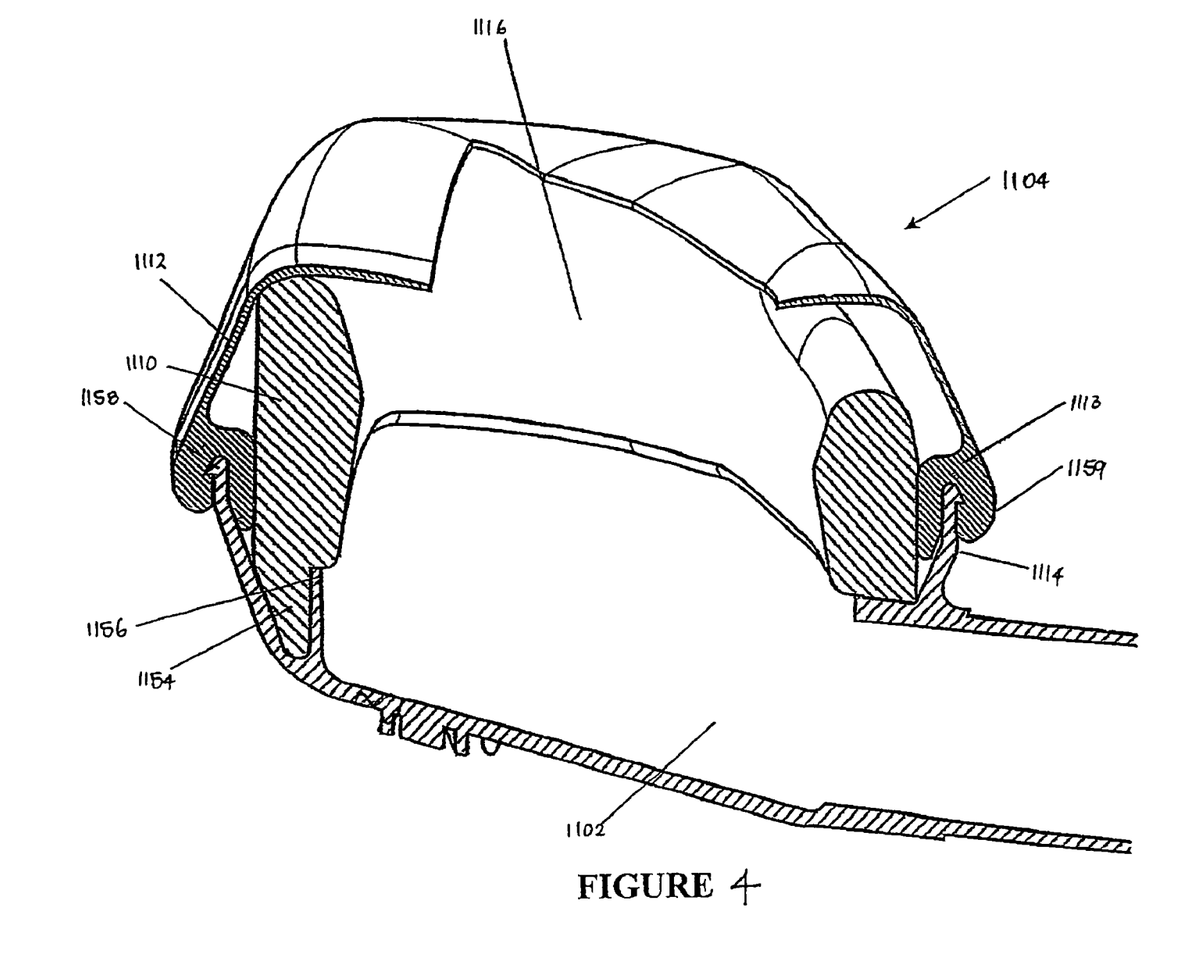
FIG. 4 is a cuttaway view of the mask of FIG. 2.

The nasal mask 100 of FIG. 2 has a cushion that is made up of an inner cushion and outer sheath or membrane. Referring now to FIGS. 3 and 4 in particular, in mask cushion 1104 as shown this cushion is provided around the periphery of the nasal mask 100 to provide an effective seal of the mask onto the face of the user in order to prevent leakage of gases being supplied to the user. The cushion 1104 is shaped to approximately follow the contours of a patient's face. The cushion 1104 will deform when pressure is applied by the headgear (not shown) to adapt to the individual contours of any particular user. In particular, there is an indented section 1150 intended to fit over the bridge of the user's nose as well as a less indented section 1152 to seal around the section beneath the nose and above the user's upper lip.

In FIG. 4 we see that the cushion 1104 is composed of an inner cushion 1110 covered by an outer sealing sheath 1112. The inner cushion 1110 is preferably constructed of a resilient material, for example, polyurethane foam or silicone, and can deform independently of the outer sealing sheath 1112 in order to enable an evenly distributed pressure along the seal around the user's face formed by the sealing sheath 1112. The inner cushion 1110 can also act as a secondary seal.

The inner cushion 1110 is located around the outer periphery 1114 of the open face 1116 of the nasal mask hollow body 1102. The open face 1116 acts as a gases delivery aperture to deliver gases to a user. Similarly the outer sheath 1112 may be commonly attached at its base 1113 to the periphery 1114 and loosely covers over the top of the inner cushion 1110.

Figure 5:
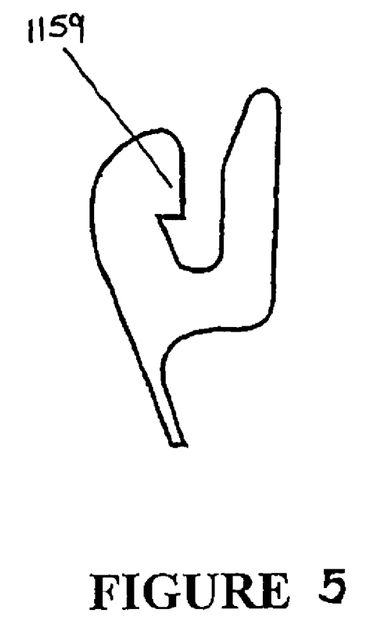
FIG. 5 is a cuttaway view of the periphery of an outer lip or sheath of the cushion of the mask of FIG. 2.
Figure 6:
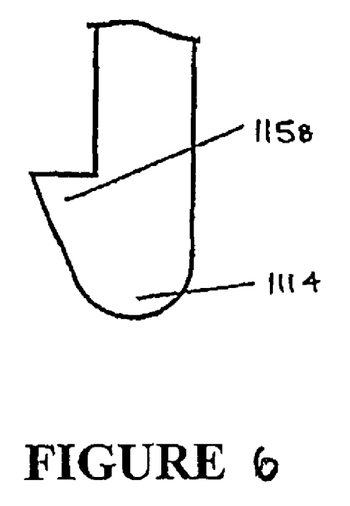
FIG. 6 is a cuttaway view of the periphery of a mask body portion of the mask of FIG. 2.

In the first embodiment as shown in FIGS. 4 to 6, the bottom of the inner cushion 1110 fits into a generally triangular cavity 1154 in the hollow body 1102. The cavity 1154 is formed from a flange 1156 running mid-way around the interior of the hollow body.

The outer sheath 1112 fits in place over the inner cushion 1110, holding it in place. The sheath 1112 is secured by a snap-fit to the periphery 1114 of the hollow body.

In FIGS. 5 and 6 the periphery 1114 is shown including an outer bead 1158. The sheath 1112 includes a matching bead 1159, whereby once stretched around the periphery 1114; the two beads (1158, 1159) engage to hold the sheath 1112 in place.

Full Face Mask

The second embodiment of the mask of the present invention is described below. The mask is a full face mask that has a gas outlet that is quieter and has a more diffused outlet flow than those of the prior art. In addition the manufacture of the gas outlet on this mask is simpler and it does not suffer to the same extent from excessive manufacturing faults. It will be appreciated that the mask as described in the second embodiment of the present invention can be used in respiratory care generally or with a ventilator but will now be described below with reference to use in a humidified CPAP system. It will also be appreciated that the outlet vent described is equally applicable to all forms of patent interface and it's use is not limited to use with full face masks, but is described below with reference to full face masks.

The full face mask of the second embodiment of the present invention also has the added benefit of extending under the chin of the patient in use, and as such patients do not require a chin strap, as is the case with some prior art masks.

Figure 7:
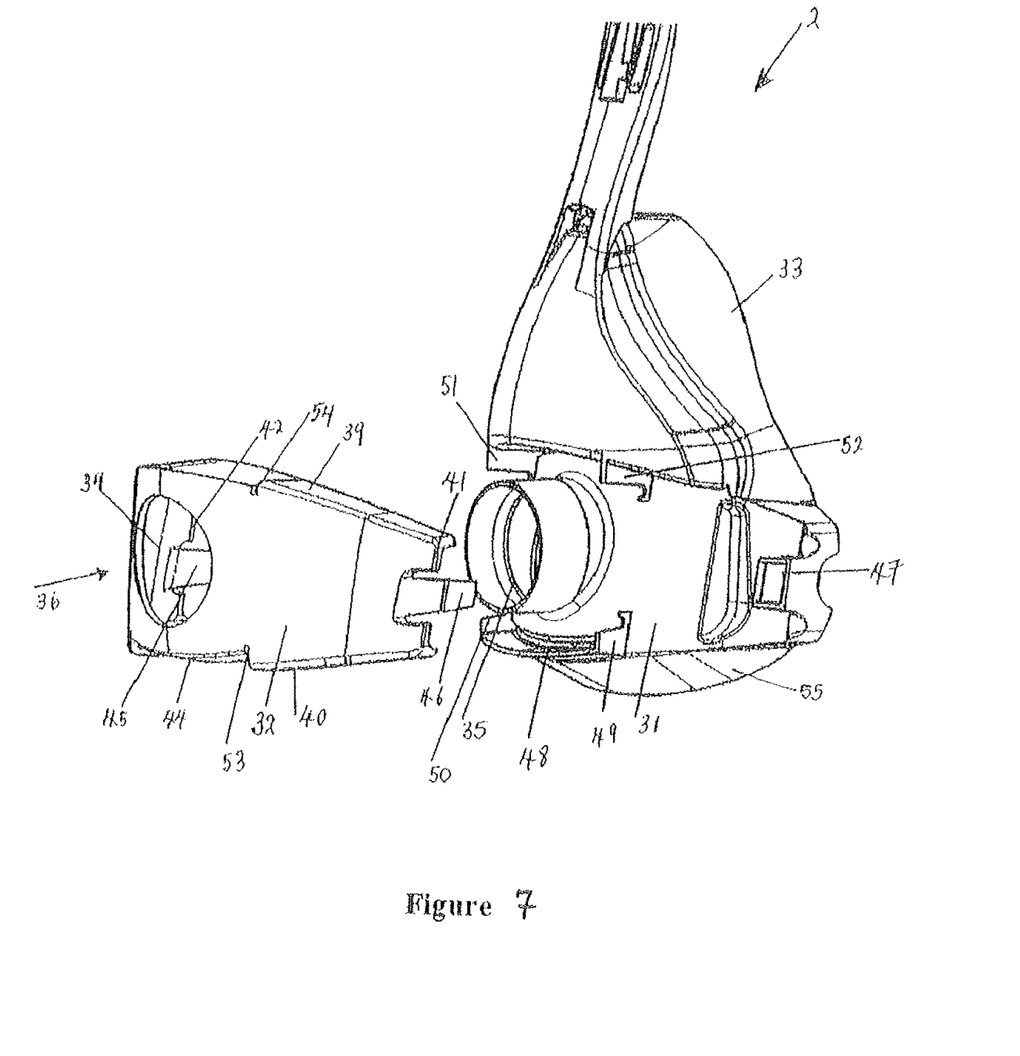
FIG. 7 is a perspective exploded view of a second embodiment of a mask of the present invention.
Figure 11:
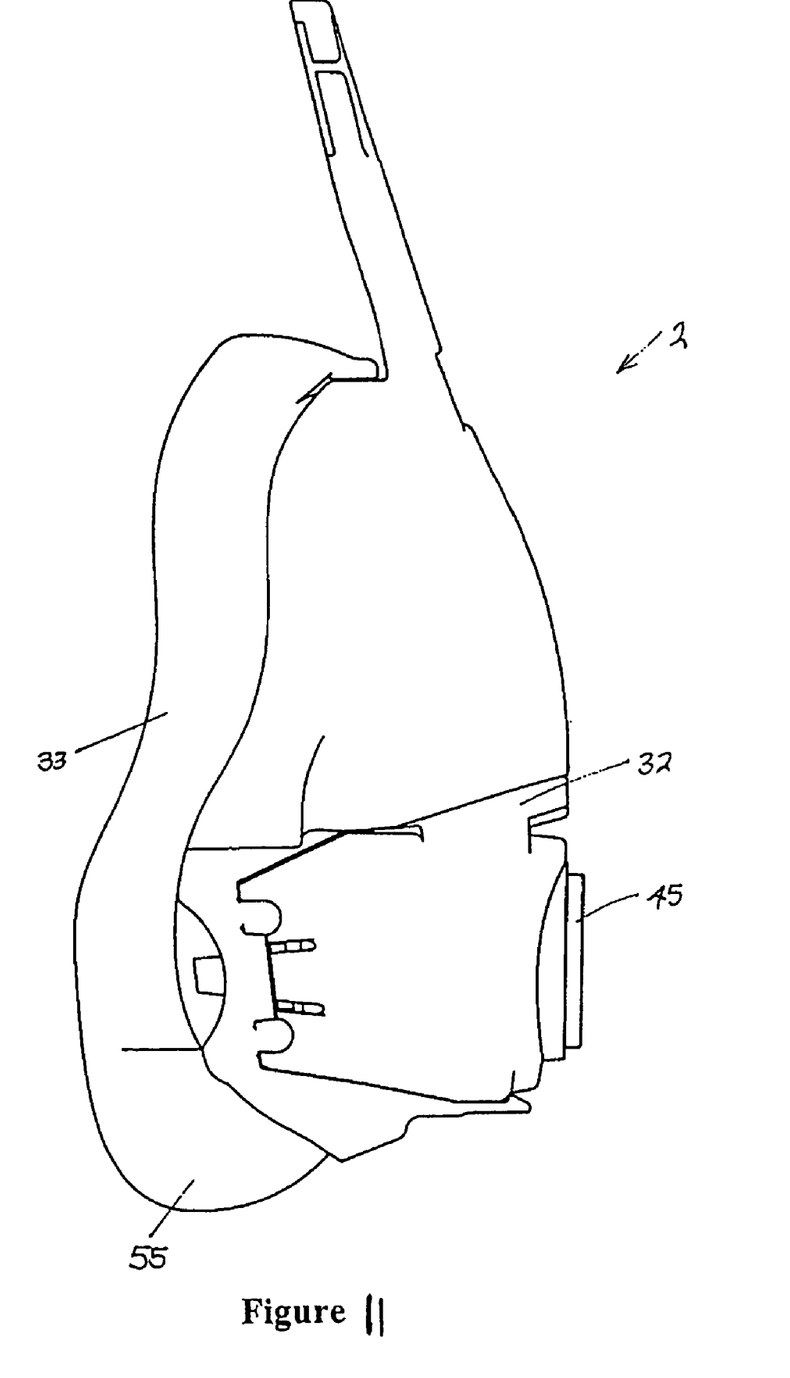
FIG. 11 is a side view of the mask of FIG. 7, where the mask is shown to have a cushion that rests in use against and users face.

Referring to FIGS. 7 and 11 a patient interface that is a full face mask is shown in detail. The mask 2 includes a hollow body 30 and mask cushion 33. The cushion 33 resides within the hollow body 30 and provides cushioning of the mask 2 or the patient's face.

The hollow body and mask cushion are shown in FIGS. 1 and 11 as extending under the patients chin, in particular, in the area indicated as 55 in FIG. 11. The extension under the chin of the cushion 33 provides a good seal and renders unnecessary a chin strap.

The hollow body 30 has an integrally formed recess 31. The recess 31 preferably extends longitudinally along and over the width of the mask body 30 but may not extend the full width of the mask as shown in FIG. 7. Further the recess 31 may not be a longitudinal recess but lateral or other orientation. An outlet member or insert 32 is fittable about or in the recess. The insert 32 substantially covers the whole of the recess 31. The recess 31 and insert 32 each have complimentary circular apertures 34, 35 that form an inspiratory inlet 36 when the insert 32 is placed in the recess 30. The inlet 36 is capable of being connected to the tubing that forms the inspiratory conduit 3 (as shown on FIG. 1). Gases, supplied to the inspiratory conduit 3 from the CPAP device and humidifier, enter the mask through the apertures 34, 35 and the patient is able to breathe these gases. The mask 2 is positioned around the nose and mouth of the user 1 and headgear (not shown) may be secured around the back of the head of the patient 1 to assist in the maintaining of the mask on the patient's face. The restraining force from the headgear on the hollow body 30 ensures enough compressive force on the mask cushion 33 to provide an effective seal against the patient's face.

The hollow body 30 and insert 32 are injection moulded in a relatively inflexible material, for example, polycarbonate plastic. Such a material would provide the requisite rigidity for the mask as well as being transparent and a relatively good insulator.

Figure 8:
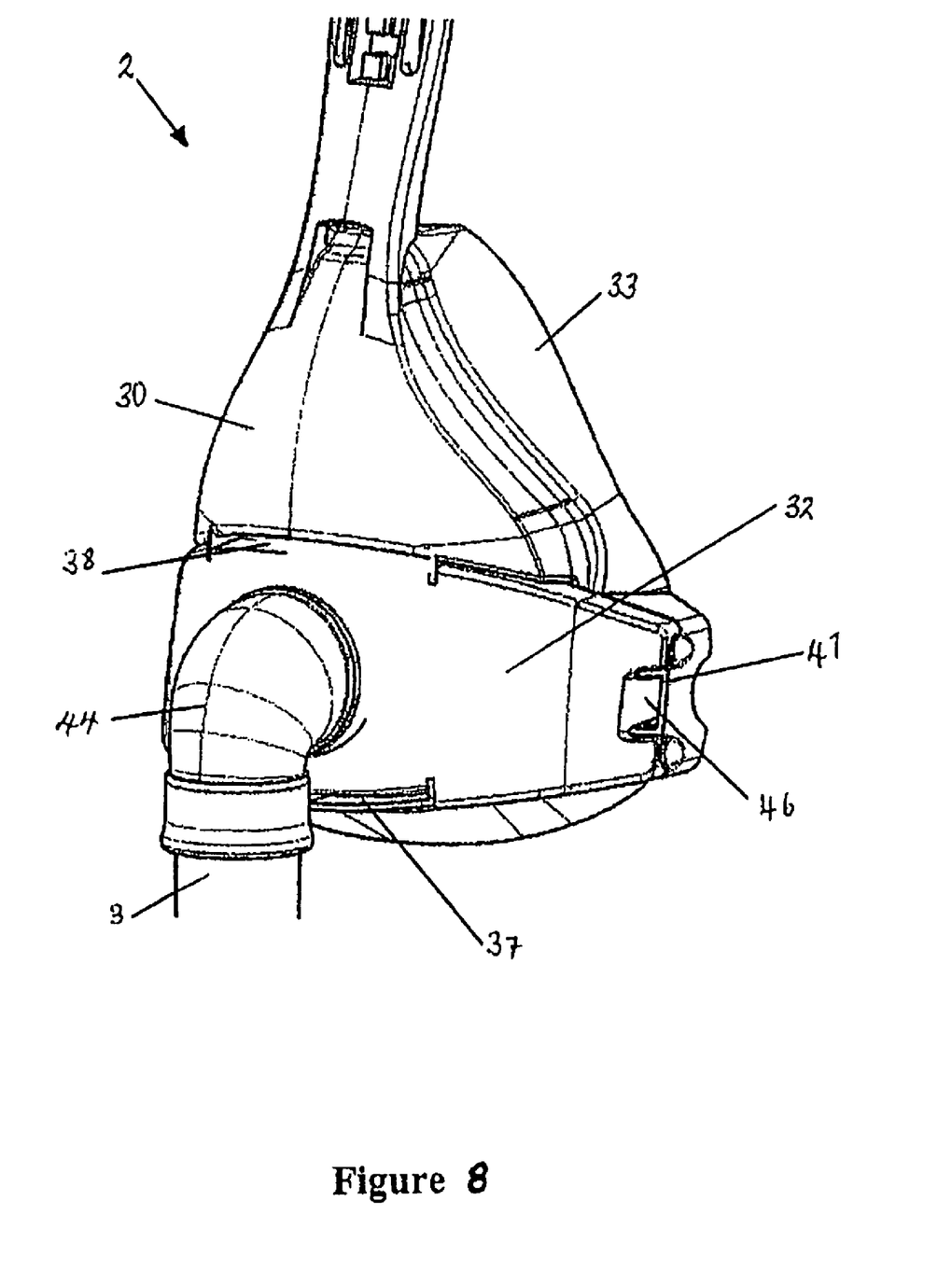
FIG. 8 is a perspective view of the mask of FIG. 7.
Figure 9:
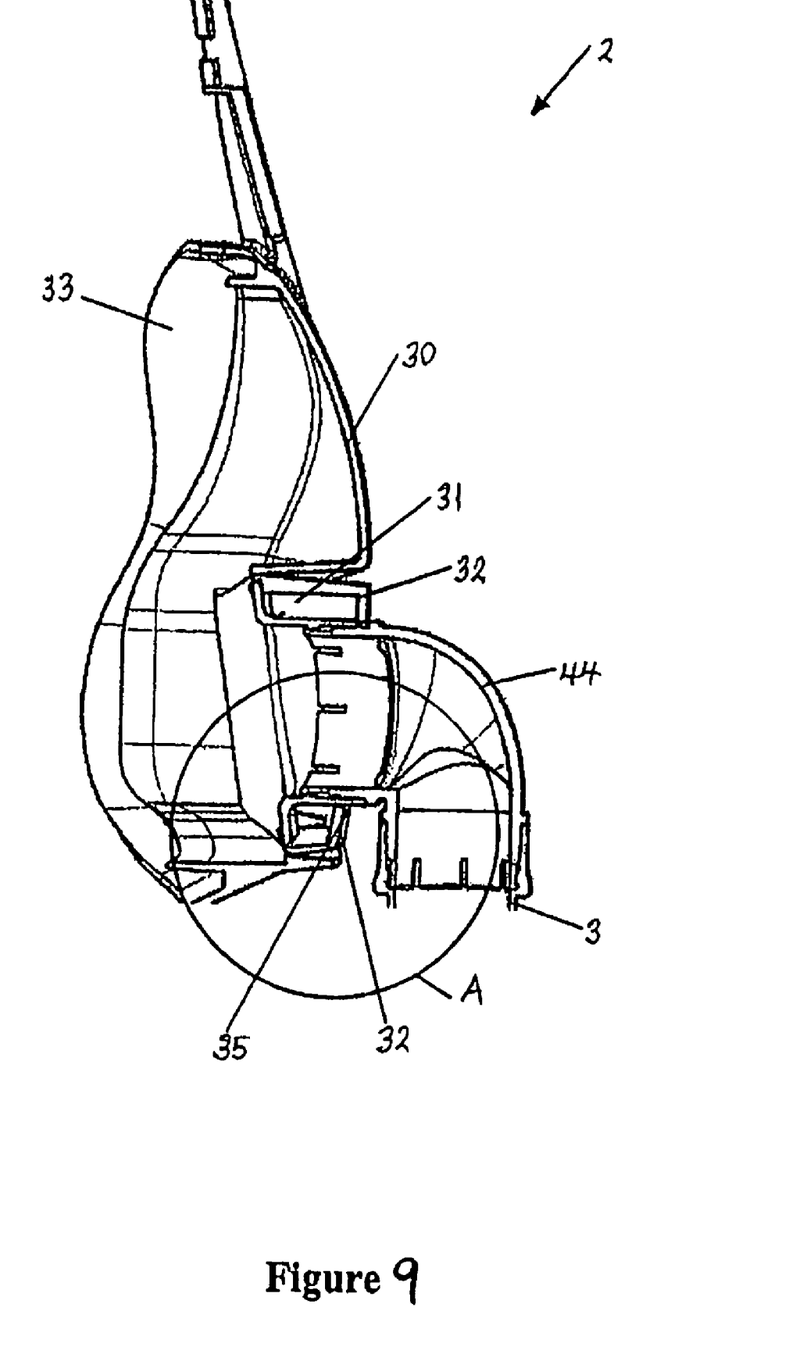
FIG. 9 is a side cross section of the mask of FIG. 7.
Figure 10:
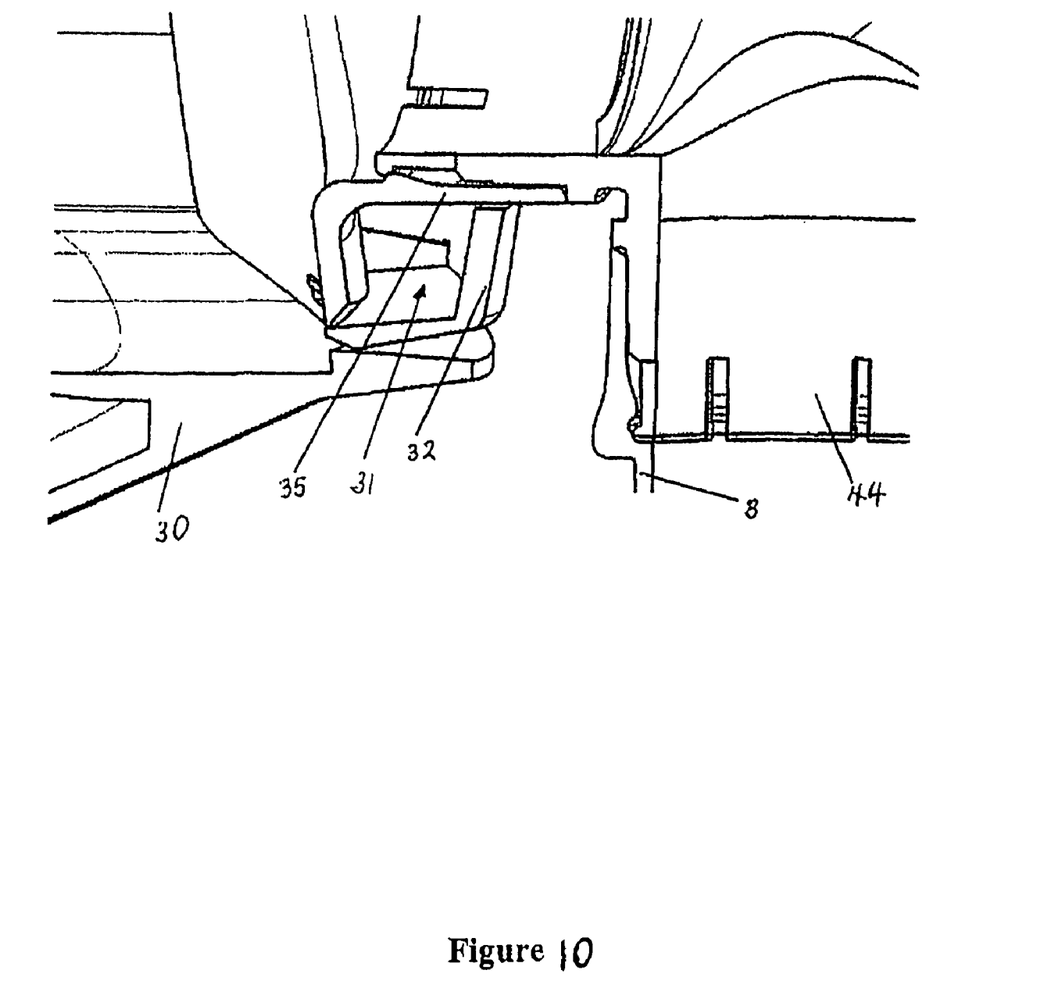
FIG. 10 is a close up view of detail A of FIG. 9.

Referring to FIG. 8, when the insert 32 is in placed on the mask shell or hollow body 30 in the recess 31 narrow slots 37, 38 are created between the mask shell 30 and insert 32. These slots 37, 38 act as expiratory vents for gases expired in use into the mask by the patient wearing the mask.

In some forms of the mask of the present invention the insert 32 is removable, but in other forms the insert is welded in place to prevent removal.

The insert 32 and narrow slots or outlet vents 37, 38 will now be described in more detail. Referring to FIGS. 7 to 11, the insert 32 is curved to follow the contours of the mask shell 30 and has upper and lower sides 39, 40 that taper down towards the left and right sides 41, 42. Two elongated recesses 53, 54 are formed on the insert's upper and lower sides 39, 40. The recesses 53, 54 are shown as being formed in the middle section of the insert 32 near to the inspiratory aperture 34 and do not extend over the full length of the upper and lower sides 39, 40. In other forms the recesses (that form the expiratory vents) may extend along the full length of the upper and lower sides of the insert. Thus, when the insert 32 is attached or connected to the mask shell 30 at the recess 31, narrow outlet vents 37, 38 are formed at the boundary between the insert 32 and mask shell 30.

To provide support to the insert 32, within the recess 31 a number of walls are provided that the insert 32 rests against. In particular, as shown in FIG. 7, a lower internal wall 48 having side walls 49, 50 extending upwards from it is formed at the lower edge of the recess 31. The lower outlet vent 37 is actually formed between the boundary of the lower wall 48 and the lower side 44 of the insert 32. Upper internal sideways walls 52, 56 are also formed in the recess 31. These provide further support and each of the side walls 49, 50, 51, 52 fit within slots (of which only two slots 53, 54 of the four slots are shown in FIG. 7).

The insert 32 may be permanently fixed in the mask shell 30 by gluing, ultrasonic welding or other appropriate fastening methods. In other forms, and particularly that shown in FIG. 7, the insert 32 is removable from the mask shell 30 and is provided with clips 45, 46. The clips 45, 46 are fastenable in apertures (of which only one side aperture 47 is shown in FIG. 7) at the sides of the mask body 30. The clips 45, 46 merely need to be pushed inwards by a user to disengage them from the apertures 47 so that the insert 32 can be removed.

FIGS. 8 to 11 show the mask 2 of the present invention in an in use form where the insert 32 is attached to the mask shell 30 and a conduit 3 that is inserted and held within the inspiratory inlet 36 and aperture formed in the insert 32 and through the mask shell 30. The conduit 3 may be connected to an elbow connector 44, which may also be capable of swiveling within the aperture.

To ensure a proper seal around the outlet vents 37, 38 and between the insert 32 and mask shell 30 a plastics gasket, for example, one made of elastomer, such as silicon, may be provided between the insert 32 and mask shell 30. The gasket (not shown) would ensure sealing between these parts and reduce the noise of gases exiting the vents 37, 38.

It will be appreciated that by providing expiratory vents in the mask of the present invention effectively allows for minimising of the noise generated by the outward flow of expiratory gases form the mask, as well as reducing the noise level, the flow through the outlet vents is more diffused.

The hollow body 30 is preferably injection moulded in a relatively inflexible material such as polycarbonate plastic. Such a material will provide rigidity for the mask be transparent and a relatively good insulator. However, other appropriate substantially rigid materials may be used for the hollow body.

The mask cushion 33 is preferably moulded in a substantially soft and resilient material, for example polyurethane foam or silicone gel.

The cushion 33 may be a single inner cushion as described above in relation to the nasal mask of the first embodiment. Alternatively, the cushion for the full face mask 2 may be comprised of an inner cushion and outer sheath. In this form of the full face mask the inner cushion would similarly be constructed of a resilient material such as polyurethane foam or silicone gel. The outer sheath attaches to the hollow body 30 over the inner cushion. The outer sheath is preferably made from a soft resilient material such as silicone; however, other appropriate materials may be used.

Figure 12:
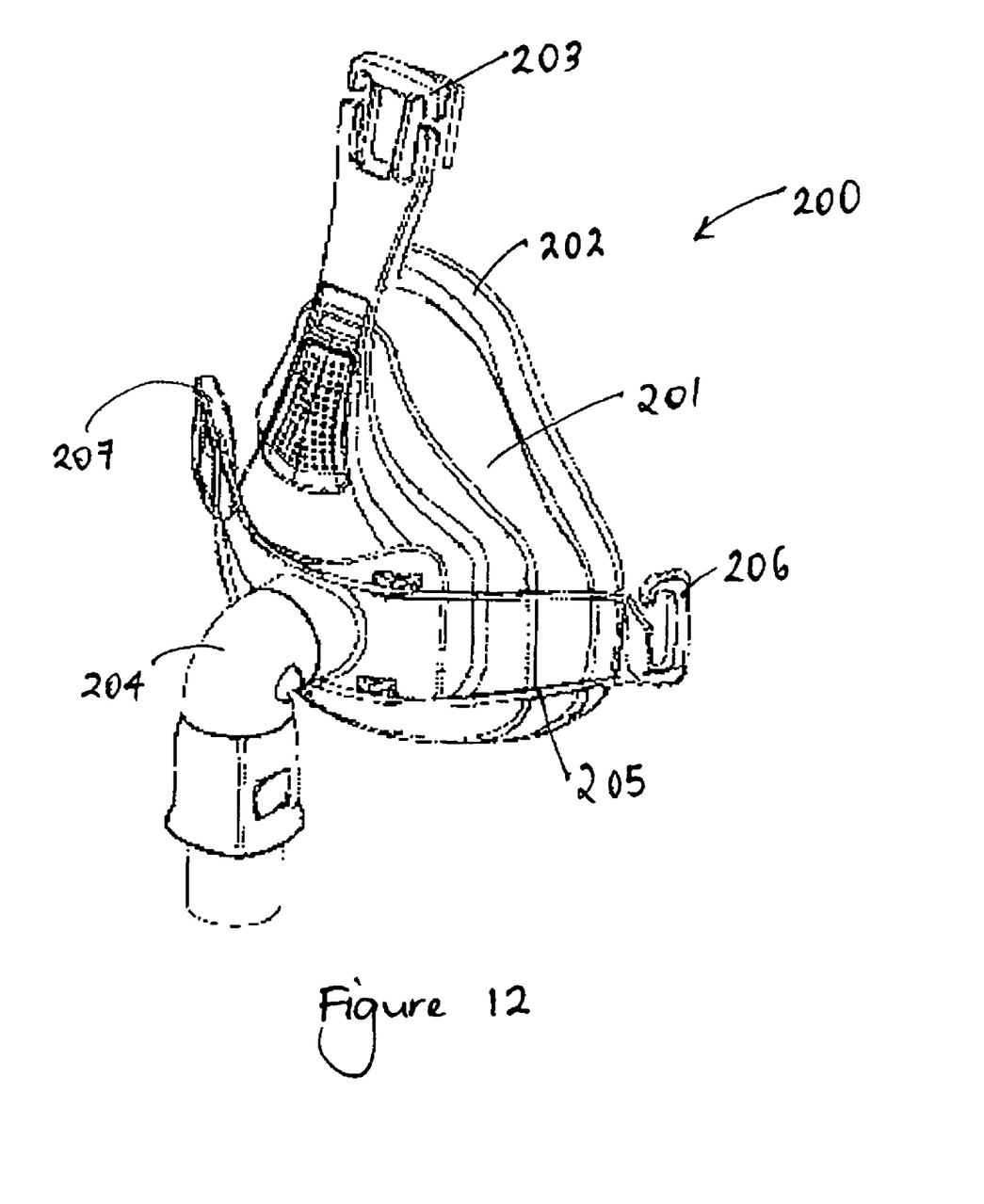
FIG. 12 is a perspective view of a mask of the third embodiment of the present invention.
Figure 13:
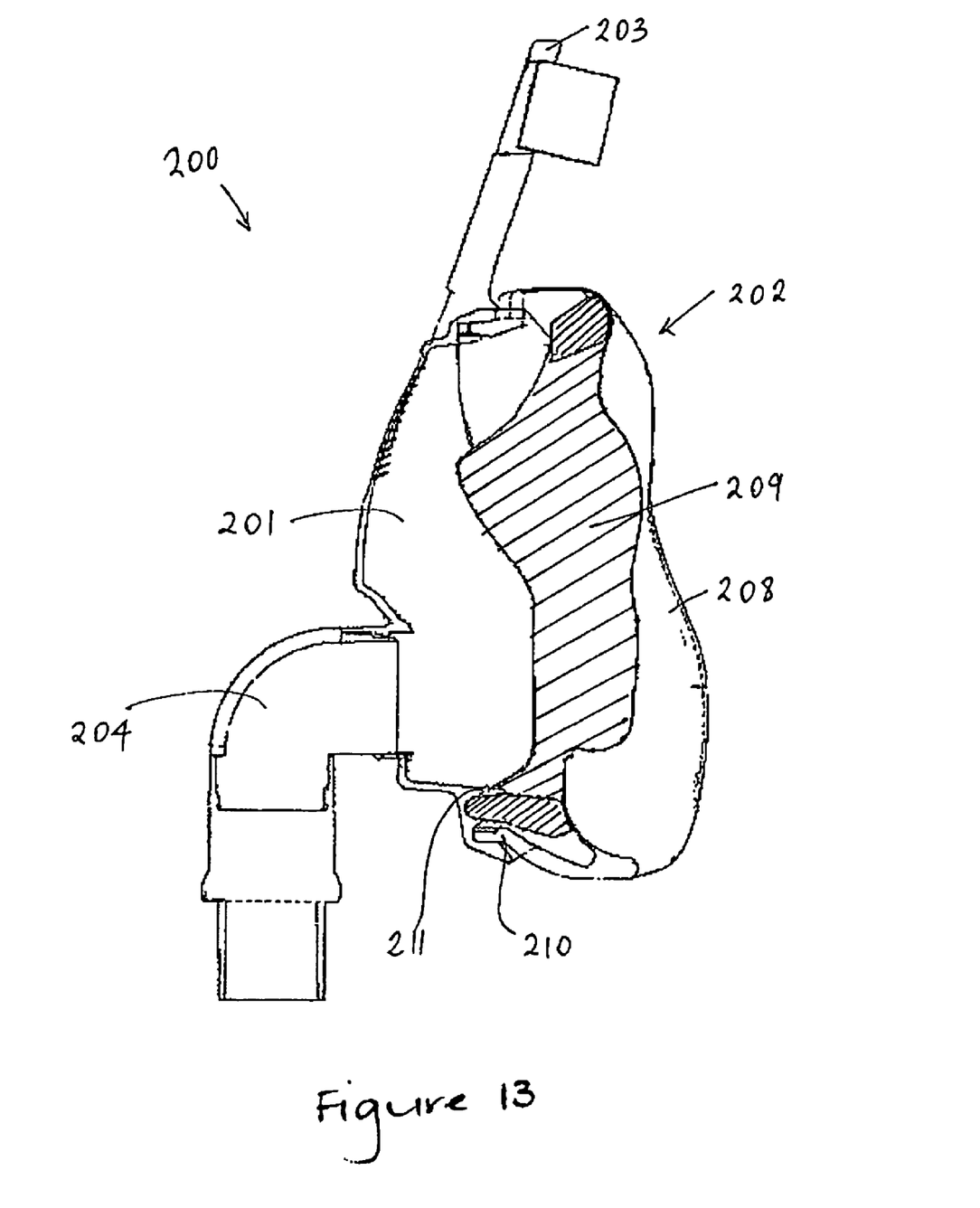
FIG. 13 is a cross sectional view of the mask of FIG. 12.

Referring now to FIGS. 12 and 13 a third embodiment of a mask of the present invention is shown. This mask also extends under a user's chin in use. The mask 200 is a full face mask similar to the mask 2 of the second embodiment. The mask 200 has a hollow body 201, cushion 202 and an inlet 204 for the receiving of gases from a CPAP system such as is described in relation to FIG. 1.

The mask 200 also has a forehead rest 203 that in use rests against the user's forehead and provides an attachment for headgear (not shown).

The mask 200 has a flexible strap 205 that removably attaches to the mask at points that allow the strap 205 to slide through, over the mask. The ends 206, 207 of the strap 205 have attachment hooks that enable attaching of headgear straps.

The cushion 202 of the mask 200 is preferably comprised of two parts; an inner resilient cushion 209 and an outer flexible sheath. These are similar to the resilient cushion and outer sheath as described above in relation to FIGS. 3 and 4 and the nasal mask of the first embodiment. The inner cushion 209 sits within a set of flanges 210 and 211 formed on the hollow body and the outer sheath 208 is attached to the hollow body's 201 periphery and loosely about the inner cushion 209.

In this manner the cushion 202 is similar to that described above in relation to the nasal mask, where the inner cushion 209 and outer sheath 208 provide sealing but enables independent deforming of each to better suit individual facial contours of the user.

The invention claimed is:

1. A device for delivering a supply of gases to a user comprising:
    a hollow body including a gases inlet and gases delivery aperture, said gases inlet in use in fluid communication with said supply of gases,
    a resilient cushion adapted to engage around or adjacent to a periphery of said gases delivery aperture, and
    a flexible sheath adapted to engage around or adjacent to the periphery of said gases delivery aperture between said resilient cushion and a user, wherein said flexible sheath is configured to extend under a chin of the user during use,
    said resilient cushion and said flexible sheath each including at least a portion shaped to approximate the facial contour of a user, wherein said resilient cushion is adapted to deform substantially independently of said flexible sheath such that said flexible sheath may be deformed without deforming the resilient cushion, wherein said resilient cushion is a foam cushion, and wherein said hollow body has a flange at least partially around the interior of said hollow body, said flange and said interior forming a cavity adapted to house in use apart of said resilient cushion.

2. A device for delivering a supply of gases to a user as claimed in claim 1 wherein said flexible sheath is of significantly higher density than that of said resilient cushion.

3. A device for delivering a supply of gases to a user as claimed in claim 1 wherein said flexible sheath is a sealing membrane substantially covering, and substantially thinner than, said resilient cushion.

4. A device for delivering a supply of gases to a user as claimed in claim 1 wherein the periphery of said gases delivery aperture and the periphery of said flexible sheath are fitted with corresponding connectors, whereby in use said flexible sheath is adapted to fit at least partially over the periphery of said hollow body, said corresponding connectors thereby in use holding said flexible sheath substantially in position on said hollow body, to assist in sealing said flexible sheath against the facial contours of a user.

5. A device for delivering a supply of gases to a user as claimed in claim 1 wherein said resilient cushion and said flexible sheath are configured to extend below a user's chin in use.

6. A device for delivering a supply of gases to a user according to claim 1 wherein said hollow body is more rigid than said sealing cushion.

7. A device for delivering a supply of gases to a user as claimed in claim 1 wherein the contours of said hollow body extend to enclose the nose and mouth of a user.

8. A device for delivering a supply of gases to a user as claimed in claim 1 wherein said hollow body is configured to extend below a user's chin.

9. A device for delivering a supply of gases to a user as claimed in claim 1 wherein said hollow body includes a flexible strap attached to it, the strap capable of sliding over said mask, said strap having two ends, each end of the strap attached to a headgear strap, the strap allowing said headgear straps to move without moving said mask.

10. A device for delivering a supply of gases to a user as claimed in claim 1 wherein said hollow body includes a plurality of flanges, said cushion retained within said flanges, said flexible sheath attached about the periphery of said hollow body and loosely attached about said cushion.

11. A device for delivering a supply of gases to a user as claimed in claim 1 wherein said cushion includes an indented section intended to fit over the bridge of the user's nose.

12. A device for delivering a supply of gases to a user as claimed in claim 1 wherein said cushion further includes a less indented section to seal around the part of the user's face under the nose and above the upper lip.

13. A device for delivering a supply of gases to a user as claimed in claim 1 wherein said device includes a forehead rest, said forehead rest adapted to rest against the forehead of the user.

14. A device for delivering a supply of gases to a user as claimed in claim 13 wherein said device further comprises headgear, said headgear secured around the back of the head of the user, the headgear exerting a restraining force on said forehead rest and said hollow body, said restraining force also acting on said cushion to provide effective sealing against the user's face.

15. A device for delivering a supply of gases to a user as claimed in claim 1 wherein said hollow body is constructed from a substantially rigid material, said hollow body also being substantially transparent.

16. A device for delivering a supply of gases to a user as claimed in claim 1 further comprising a gap between the resilient cushion and the flexible sheath.

17. A device for delivering a supply of gases to a user as claimed in claim 1 further comprising a forehead rest that is operably connected to the hollow body.

18. A device for delivering a supply of gases to a user as claimed in claim 1 wherein the hollow body includes an inlet connected to a heated inspiratory conduit.

19. A device for delivering a supply of gases to a user as claimed in claim 1 wherein the flexible sheath is attached to the hollow body via a snap fit.

20. A device for delivering a supply of gases to a user as claimed in claim 1 wherein said flexible sheath substantially surrounds the resilient cushion.

21. A device for delivering a supply of gases to a user as claimed in claim 1 wherein said resilient cushion is directly in contact with an inner surface of the hollow body.

22. A device for delivering a supply of gases to a user as claimed in claim 1 wherein a portion of said resilient cushion is retained in a cavity formed by a flange extending from the hollow body and a periphery of the hollow body.

* * * * *